United States Patent
Seligman et al.

(10) Patent No.: US 9,795,795 B2
(45) Date of Patent: Oct. 24, 2017

(54) DEVICE AND CIRCUITRY FOR CONTROLLING DELIVERY OF STIMULATION SIGNALS

(75) Inventors: Peter Misha Seligman, Essendon (AU); Hugh Joseph McDermott, Mt Macedon (AU)

(73) Assignee: The Bionics Institute of Australia, Victoria (AU)

( * ) Notice: Subject to any disclaimer, the term of this patent is extended or adjusted under 35 U.S.C. 154(b) by 669 days.

(21) Appl. No.: 14/235,685

(22) PCT Filed: Jul. 25, 2012

(86) PCT No.: PCT/AU2012/000886
§ 371 (c)(1),
(2), (4) Date: May 27, 2014

(87) PCT Pub. No.: WO2013/013269
PCT Pub. Date: Jan. 31, 2013

(65) Prior Publication Data
US 2014/0277274 A1    Sep. 18, 2014

Related U.S. Application Data

(60) Provisional application No. 61/512,755, filed on Jul. 28, 2011.

(30) Foreign Application Priority Data

Jul. 28, 2011    (AU) .................... 2011903009

(51) Int. Cl.
*A61N 1/36*    (2006.01)
*A61N 1/372*    (2006.01)

(52) U.S. Cl.
CPC ...... *A61N 1/37241* (2013.01); *A61N 1/36032* (2013.01); *A61N 1/36046* (2013.01); *A61N 1/36142* (2013.01)

(58) Field of Classification Search
CPC ............ A61N 1/37241; A61N 1/36032; A61N 1/36046; A61N 1/36142
(Continued)

(56) References Cited

U.S. PATENT DOCUMENTS 6,035,237 A    3/2000  Schulman et al.
7,801,600 B1   9/2010  Carbunaru et al.
(Continued)

OTHER PUBLICATIONS

"International Application No. PCT/AU2012/000886, International Search Report and Written Opinion dated Aug. 13, 2012", (Aug. 13, 2012), 8 pgs.

*Primary Examiner* — Catherine Voorhees
(74) *Attorney, Agent, or Firm* — Schwegman Lundberg & Woessner, P.A.

(57) ABSTRACT

Some embodiments relate to a device for generating stimulation signals, comprising: a stimulation delivery circuit; a first component to monitor charge delivered in at least one charge pulse via the stimulation delivery circuit; and a second component to ensure delivered charge substantially corresponds to charge of a charge pulse intended to be delivered by the stimulation delivery circuit. In some embodiments, the device may further comprise a charge setting circuit responsive to a charge pulse setting signal, such as a constant current of fixed pulse width, to set the charge of the charge pulse intended to be delivered.

22 Claims, 4 Drawing Sheets

(58) Field of Classification Search
USPC .......................................................... 607/55
See application file for complete search history.

(56) References Cited

U.S. PATENT DOCUMENTS

| | | | |
|---|---|---|---|
| 2007/0135868 A1 | 6/2007 | Shi et al. | |
| 2010/0023070 A1* | 1/2010 | Moffitt | A61N 1/36071 607/2 |
| 2011/0160799 A1* | 6/2011 | Mishra | A61N 1/36032 607/57 |
| 2012/0277830 A1* | 11/2012 | Arfin | A61N 1/36146 607/62 |

* cited by examiner

DEVICE AND CIRCUITRY FOR CONTROLLING DELIVERY OF STIMULATION SIGNALS

PRIORITY CLAIM TO RELATED APPLICATIONS

This application is a national stage application under 35 U.S.C. §371 of PCT/AU2012/000886, filed Jul. 25, 2012, and published as WO 2013/013269 A1 on Jan. 31, 2013, which claims priority to U.S. Provisional Application Ser. No. 61/512,755, filed Jul. 28, 2011, and to Australian Application No. 2011903009, filed Jul. 28, 2011, which applications and publication are incorporated by reference as if reproduced herein and made a part hereof in their entirety, and the benefit of priority of each of which is claimed herein.

TECHNICAL FIELD

Described embodiments generally relate to devices, circuitry and prostheses for controlling delivery of stimulation signals to excitable tissue, such as nerves and muscles.

BACKGROUND

Biphasic current stimulation is widely used in electrical stimulation of neurons. This constant current form of stimulation has an advantage that the stimulation is largely unaffected by changes in electrode impedance which occur at the interface between the signal conductors and the tissue.

The voltage required to stimulate an electrode is the product of the stimulation current and the electrode impedance in a similar way to Ohms law, which states that the voltage across a resistance is equal to the product of resistance and current. In the case of a biological stimulating electrode, the impedance is not a pure resistance but has capacitive or capacitance-like properties. Electrode impedance varies from electrode to electrode and over time.

For constant-current stimulation using rectangular biphasic pulses, the so-called impedance is defined as the voltage at a stimulation electrode at the end of the first phase of a stimulation pulse divided by the electrode current. While Ohms law applies strictly to pure resistance, the same principle is applied to calculate the voltage required to obtain a particular stimulation current.

A disadvantage of using constant current to generate the biphasic stimulation signals is that the signal generation circuitry does not always generate sufficient voltage in order to deliver the desired amount of charge to the tissue. FIG. 1 is a graph of voltage required at the signal generation circuit versus percentage of electrodes operating within voltage compliance for adults and children using aural prostheses that employ biphasic current stimulation. FIG. 1 shows that for some situations, a larger voltage is required in order to deliver the necessary charge than for other situations. Additionally, it is evident from FIG. 1 that, for much of the time, the maximum voltage level is not required in order to achieve charge delivery compliance and so a lower voltage would suffice.

The provision of a higher voltage (i.e. around 10 volts) to cater for the relatively small number of occasions that it is needed results in a far higher power consumption than is actually delivered to the electrodes, with the rest being absorbed in the current source. This power consumption has a significant effect on battery life for prostheses employing biphasic current stimulation.

It is desired to address or ameliorate one or more shortcomings or disadvantages associated with prior techniques for delivery of biphasic stimulation to excitable tissue, such as nerves and/or muscles or to at least provide a useful alternative thereto.

SUMMARY

Some embodiments relate to a device for generating stimulation signals, comprising:
- a stimulation delivery circuit;
- a first component to monitor charge delivered in at least one charge pulse via the stimulation delivery circuit; and
- a second component to ensure delivered charge substantially corresponds to charge of a charge pulse intended to be delivered by the stimulation delivery circuit.

In some embodiments, the device may further comprise a charge setting circuit responsive to a charge pulse setting signal, such as a constant current of fixed pulse width, to set the charge of the charge pulse intended to be delivered. The charge setting circuit may comprise a first current mirror circuit coupled to the second component to communicate to the second component the charge of the charge pulse intended to be delivered. The device may further comprise a reference capacitor to store the set charge.

The device may further comprise a comparator to output a difference signal indicative of difference between delivered charge from the stimulation delivery circuit and the charge intended to be delivered.

The first and second components may form at least part of a stimulation supply circuit of the device, wherein the stimulation supply circuit is coupled to provide the at least one charge pulse to the stimulation delivery circuit.

The device may further comprise a delivered charge capacitor to store charge corresponding to an amount of charge delivered during delivery of the at least one charge pulse. The device may further comprise a transistor in series with the delivered charge capacitor and an output of a second current mirror arrangement coupled to a current supply input of the device.

The device may further comprise a third component responsive to the second component to extend the at least one charge pulse until the intended charge is delivered.

Some embodiments relate to a device for generating stimulation signals, comprising:
- a stimulation delivery circuit;
- a monitoring component to monitor charge delivered in at least one charge pulse via the stimulation delivery circuit; and
- a feedback component to provide a feedback signal so that delivered charge substantially corresponds to charge of a charge pulse intended to be delivered by the stimulation delivery circuit.

The feedback component may comprise a charge setting circuit responsive to a charge pulse setting signal to set the charge of the charge pulse intended to be delivered. The feedback component may comprise a comparison circuit, and wherein the charge setting circuit comprises a first current mirror circuit coupled to the comparison circuit to indicate to the comparison circuit the charge of the charge pulse intended to be delivered. The feedback component comprises a reference capacitor to store the set charge. The at least one charge pulse may be delivered to one or more nerves or to the vicinity of one or more nerves.

The comparison circuit may comprise a comparator to output a difference signal indicative of difference between delivered charge from the stimulation delivery circuit and the charge intended to be delivered.

The monitoring component and feedback component may form at least part of a stimulation supply circuit of the device, wherein the stimulation supply circuit is coupled to provide the at least one charge pulse to the stimulation delivery circuit.

The device may further comprise a delivered charge capacitor to store charge corresponding to an amount of charge delivered during delivery of the at least one charge pulse. The device may further comprise at least one transistor in series with the delivered charge capacitor and forming part of a second current mirror arrangement coupled to a current supply input of the device.

The device may further comprise a pulse extension component responsive to the feedback component to extend the at least one charge pulse until the intended charge is delivered.

The device may further comprise a microcontroller coupled to the device components to control pulse timing and pulse width of the at least one charge pulse.

Some embodiments relate to control circuitry to control delivery of stimulation signals to a stimulus site, comprising:
monitoring circuitry to monitor charge delivered in at least one charge pulse to an output coupled for delivery of the charge to the stimulus site; and
compliance circuitry cooperating with the monitoring circuitry to ensure delivery of charge intended to be delivered in a charge pulse based on the monitored delivered charge.

Some embodiments relate to control circuitry for controlling delivery of stimulation signals, comprising:
stimulation delivery circuitry;
monitoring circuitry to monitor charge delivered in at least one charge pulse via the stimulation delivery circuitry; and
feedback circuitry to provide a feedback signal so that delivered charge substantially corresponds to charge of a charge pulse intended to be delivered by the stimulation delivery circuitry.

The at least one charge pulse may form part of a series of charge pulses to be delivered as charge-balanced pulsatile stimulation, which may be in the form of a bi-phasic stimulus pulse, for example. Where the at least one charge pulse includes bi-phasic stimulus pulses, the second phase may be the same as the first phase or it may be different. Where the second phase is different, it may use a higher current or rely on voltage-driven stimulation, for example.

The device or circuitry may be configured for use as part of a prosthesis or assistive device. The prosthesis may be a sensory prosthesis, such as an auditory or visual prosthesis. In other embodiments, the prosthesis may be a cardiac prosthesis or another prosthesis for delivering myoelectric stimulation. In some embodiments, the device or circuitry may form part of a device for stimulation of a selected part of the brain, for example to modulate, hinder or otherwise beneficially affect various brain disorders, particularly including but not limited to movement disorders, psychiatric disorders, seizures or potential seizures. Such seizures may be associated with epilepsy or Parkinson's disease, for example.

Some embodiments relate to a prosthesis (or a similar type of medical bionics device) comprising the described device and/or circuitry and/or configured to perform the described method.

Some embodiments relate to a method for controlling delivery of stimulation signals, comprising:
delivering at least one charge pulse via a stimulation delivery circuit;
monitoring charge delivered in at least one charge pulse via the stimulation delivery circuit; and
providing a feedback signal so that delivered charge substantially corresponds to charge of a charge pulse intended to be delivered by the stimulation delivery circuit.

BRIEF DESCRIPTION OF THE DRAWINGS

Embodiments are described in further detail below, by way of example and with reference to the accompanying drawings, in which.

DETAILED DESCRIPTION

Figure 1:
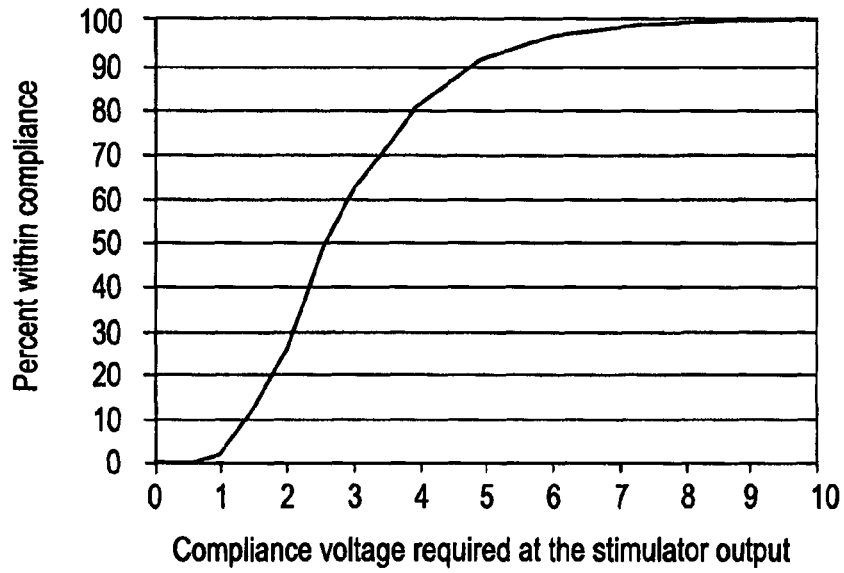
FIG. 1 is a graph of compliance voltage required at a stimulator output versus percentage within compliance for biphasic current stimulation devices.
Figure 2:
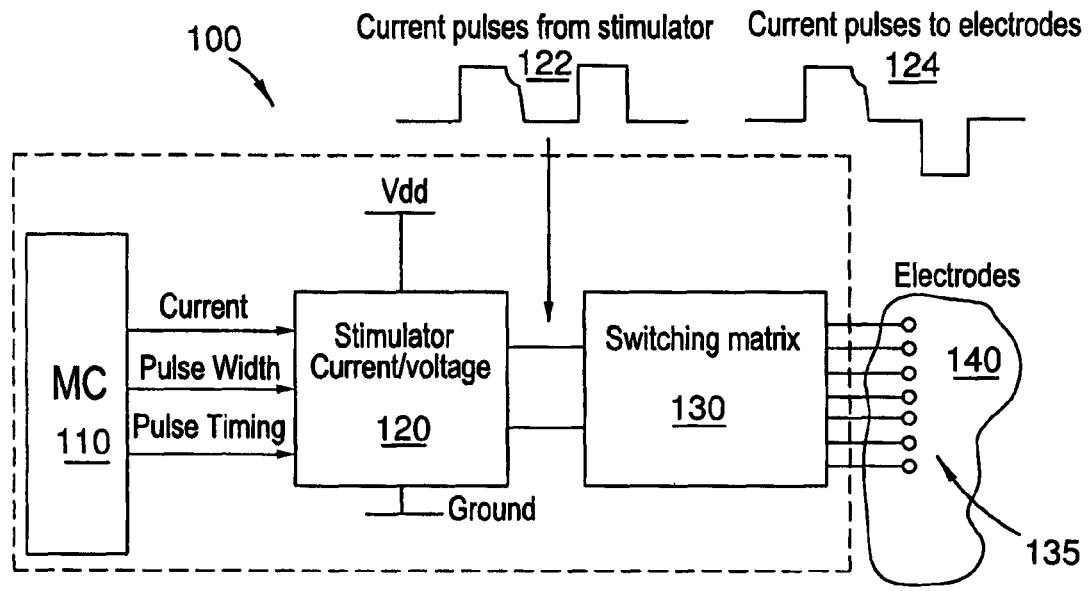
FIG. 2 is a schematic illustration of a device for generating stimulation signals as part of a prosthesis.

Described embodiments generally relate to devices, circuitry and prostheses for generating nerve stimulation signals. In described embodiments, stimulation to be delivered by the described devices and/or circuitry is to be delivered subcutaneously, rather than transcutaneously. However, the principles of operation of described embodiments are applicable to other modes of electrical stimulation of different kinds of excitable human and/or animal tissue.

In some embodiments, the stimulation signals may be generated based on an external stimulus, such as an auditory or visual stimulus. However, in some embodiments, the stimulation signals may not have any external trigger and may be generated responsive to sensed internal physiological conditions or to a predetermined timing sequence accessible to a processor of the device.

Embodiments have particular applicability to bi-phasic current stimulation regimes and this is therefore the context in which embodiments are generally described. However, the emphasis throughout on biphasic stimulation should not be construed to limit the generalisation of the disclosure; the same functional concepts apply well to mono-phasic or tri-phasic or other stimulation waveforms. In each case, charge balance is required at each electrode and can be achieved by known techniques. The provision of charge pulses may therefore be described in terms of charge-balanced pulsatile stimulation, independent of how many phases are used to deliver the stimulation.

Particular embodiments described herein are generally configured to provide monitoring and compensation or compliance functionality for stimulation devices, whereby one or more components are configured to monitor the charge provided to a stimulation delivery component for delivery to a stimulation site, such as excitable tissue, and to then take action to ensure that the intended charge (or a close enough approximation thereto) is actually delivered. In described embodiments, this is accomplished by extending the stimulation pulse until the delivered charge is substantially the same as the charge that is set as the intended amount of charge to be delivered.

Referring in particular to FIGS. 2 to 6, a stimulation device 100 is shown and described in further detail. The stimulation device 100 may also be considered as a system or subsystem of components and circuits and as part of a larger stimulation system 10. Device 100 has a microcontroller 110 that provides current, pulse width and pulse timing signals to a stimulation circuit 120, which in turn provides electrical output signals 122 (in the form of a charge pulse waveform) to switching matrix 130 for delivery of the electrical signals in biphasic form 124 to a tissue or tissue region 140 via electrodes 135 embedded in or contacting the tissue 140.

Microcontroller 110 is referenced as one non-limiting example of an electronic control component that can be used to perform the functions described herein. Other examples of possibly suitable electronic control components to perform the described functions include, but are not limited to, a microprocessor, a digital signal processor, an application-specific integrated circuit (ASIC), a state machine, a field-programmable gate array (FPGA) or a combination of any of those devices with microcontroller 110 or a combination of any two or more of such devices.

Stimulation device 100 may form part of a prosthesis 50 or other assistive device (FIG. 6) for providing nerve stimulation to nerves in the tissue 140. For convenience, the term prosthesis will be used herein in relation to reference numeral 50, but, it is to be understood that reference numeral 50 may represent assistive devices or parts thereof that do not strictly act as a prosthesis or part thereof.

The prosthesis 50 may form part of a stimulation system 10 and may include other components, such as control components 60 and power supply 70, interacting with the prosthesis 50 in order to provide appropriate control functions and power to the prosthesis 50. Power supply 70 provides power to stimulation device 100 and control components 60. Each of microcontroller 110, stimulation circuit 120 and switching matrix 130 may be coupled to a voltage supply rail Vdd and to a ground rail. The supply voltage Vdd is derived from electrical potential supplied by the power supply 70. Alternatively, microcontroller 110 may supply power to stimulation circuit 120 or control the supply of power to stimulation circuit 120 by power supply 70.

In some embodiments, the prosthesis 50 may be generally contained by a unitary housing. In other embodiments, the prosthesis 50 may comprise an implantable part 54 and a non-implantable part 52. In such two-part embodiments, the implantable part 54 includes the stimulation device 100 and at least part of power supply 70. The power supply 70 may be either self-contained or one part of a two-part power supply. Such a two-part power supply includes a power source, such as a battery, in a first part arranged to inductively transfer power to the second part and is advantageous for two-part prostheses where it is preferred to avoid having a power source in the part to be implanted. Thus, the part of power supply 70 that is in implantable part 54 may be inductively driven by an external coil in the non-implantable part 52 that houses the remainder of power supply 70. In two-part prosthesis embodiments, the control components 60, which may be used to configure stimulation settings for example, may be divided between the two parts 52, 54, with communication between the two effected by suitable communication means, preferably wirelessly.

Although some device configurations are described, various other configurations are possible. For example, the electronics could be outside and the electrodes inside the body, with a hard-wired connector linking them. Similarly, there are various ways of powering such devices. Thus, the described arrangements are intended to be exemplary and non-limiting.

The prosthesis or assistive device 50 may be employed to provide stimulation to sensory nerves, for example as part of an auditory or visual prosthesis, or to provide myoelectric stimulus for muscle activation, for example as part of a cardiac prosthesis. The prosthesis or assistive device 50 may be arranged for stimulation of a selected part of the brain, for example to modulate, hinder or otherwise beneficially affect various brain disorders, including movement disorders, psychiatric disorders, seizures or potential seizures. Such seizures may be associated with epilepsy or Parkinson's disease, for example.

The microcontroller 110 of stimulation device 100 may comprise any suitable processing device for receiving input signals, processing stored instructions and generating suitable output signals. The microcontroller 110 has suitable volatile memory and has (or at least has access to) non-volatile memory storing program code executable by the microcontroller 110 to perform the functions described herein. Such program code may be arranged as a plurality of code modules to perform certain functions, such as the monitoring and compliance functions described herein. Microcontroller 110 may receive electrical power from power supply 70 within prosthesis 50 and may supply power to stimulation circuit 120 or control the supply of power to stimulation circuit 120 by power supply 70.

Figure 3:
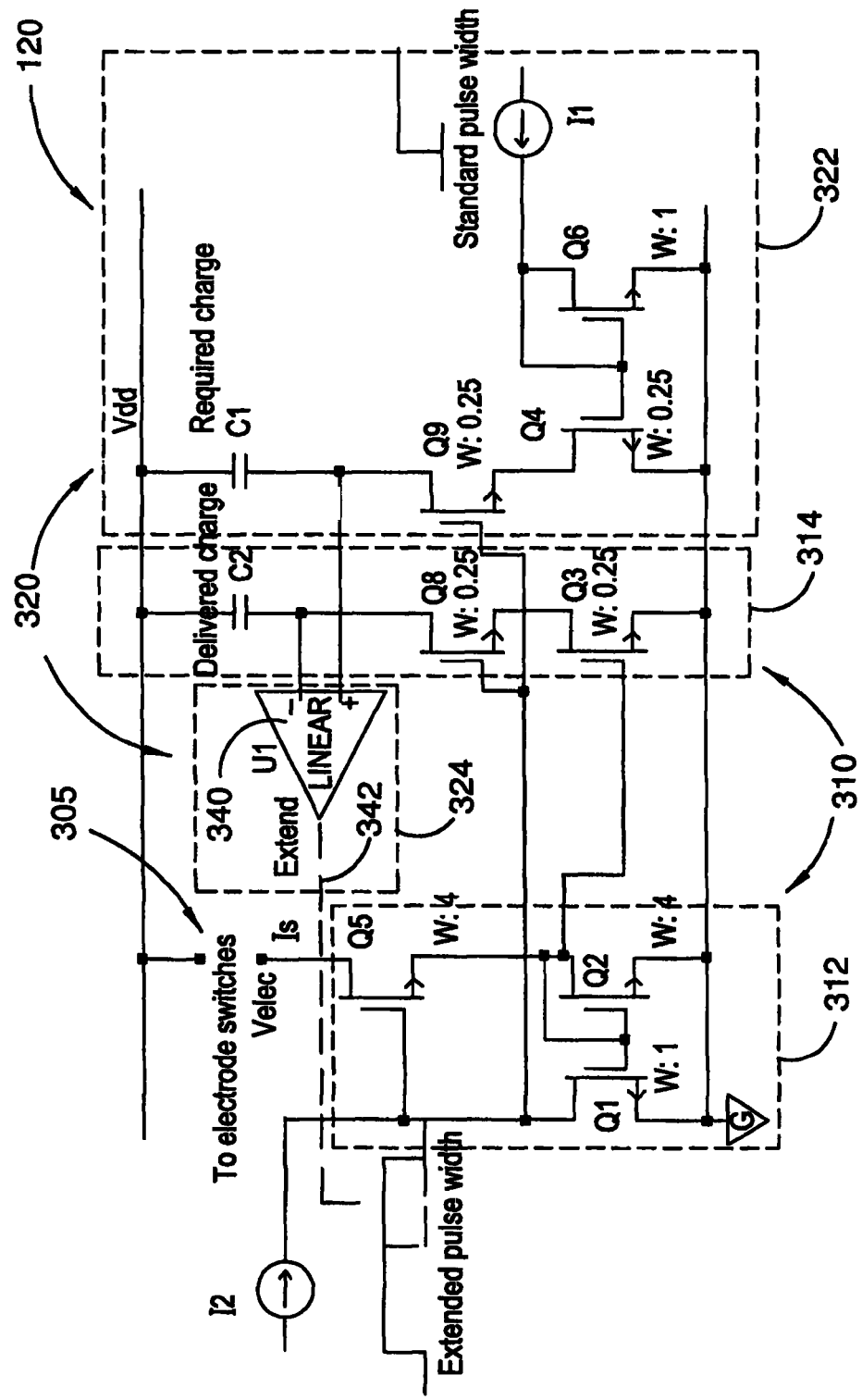
FIG. 3 is a schematic representation of circuitry for stimulation signal delivery by the device of FIG. 2.

Stimulation circuit 120 is shown in greater detail in FIG. 3. Stimulation circuit 120 receives a supply voltage Vdd at a supply rail and is effectively grounded by a return rail. Stimulation circuit 120 has a monitoring component 310 and a feedback component 320 which co-operate to monitor charge supplied to output electrodes at terminals 305 according to a voltage Velec and stimulation current Is.

Monitoring component 310 comprises a supply circuit 312 comprising a Wilson current mirror with a set current gain. In the example illustrated in FIG. 3, the current gain of the Wilson current mirror made up of transistors Q1, Q2 and Q5 is 4. Supply circuit 312 receives a reference current I2 as a current supply to drive the stimulation current Is through the output electrodes 305. The Wilson current mirror of supply circuit 312 also drives a transistor Q3 in a monitoring circuit 314 that includes a delivered charge capacitor C2 coupled to the voltage supply rail and arranged to store a measure of the charge supplied via terminals 305.

Feedback component 320 comprises a charge setting circuit 322 and a feedback circuit 324. Switching circuit 500 (FIG. 5) may also be considered to form part of feedback component 320. The charge setting circuit 322 receives a reference current $I_1$ derived from the same current source as reference current $I_2$ but separately gated therefrom so that each reference current source $I_1$, $I_2$ can independently produce one phase of charge-balanced pulsatile stimulation, such as a biphasic pulse (at the same or opposite polarisation). Reference current feeds into a current mirror made up of transistors Q4 and Q6 to charge a reference capacitor C1 with the amount of charge to be delivered according to the preset pulse width provided by current source $I_1$. Capacitors C1 and C2 may have substantially the same capacitance, although in some implementations the capacitances may be different.

Capacitor C1 may be considered to form part of feedback circuit 324 or part of charge setting circuit 322, although it is illustrated in FIG. 3 as part of the latter. Capacitor C1 acts as a reference capacitor for a comparator 340 in feedback circuit 324. Comparator 340 is coupled to capacitors C1 and C2 and arranged to output a signal indicative of the difference between the charges stored in those capacitors, as a feedback signal 342. This feedback signal 342 is used to determine whether supply of current by current supply $I_2$ should be extended in order to deliver the intended amount of charge at terminals 305 (i.e. where that is different from the charge indicated as being delivered by capacitor C2).

Transistors Q1 to Q6 may be field effect transistors (FETs), for example. However, other types of transistor may be used instead to achieve a similar effect.

Optionally, stimulation circuit 120 may include additional transistors, such as FETs Q8 and Q9, in series with the delivered charge and reference capacitors C2 and C1, respectively, to cause transistors Q3 and Q4 to more accurately mimic the voltage at transistors Q5 and Q2 of the Wilson current mirror circuit. FETs Q8 and Q9 are also in series with the respective outputs of the current mirror circuits of the supply circuit 312 and the charge setting circuit 322.

Figure 4:
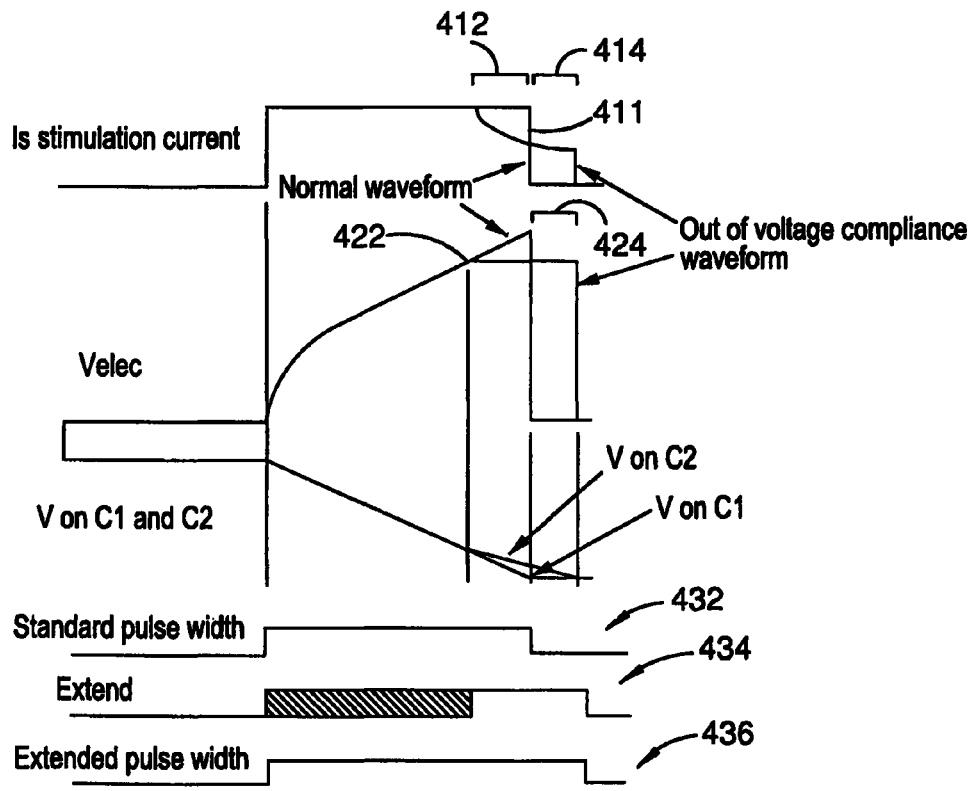
FIG. 4 is an illustration of example stimulation signal waveforms to illustrate functions of the circuitry of FIG. 3.

FIG. 4 illustrates example current and voltage waveforms provided at terminals 305 by stimulation circuit 120 and showing a putative normal waveform (i.e. where the voltage Velec delivered by the stimulation circuit complies with the voltage required by the set stimulation current) versus current and voltage waveforms where the voltage is below the compliance voltage of the current generator. In the illustrated example, the voltage Velec reaches a maximum at a point 422 (e.g. due to circuit constraints) during delivery of the standard pulse width 432, which, as illustrated in relation to the delivery of the stimulation current, results in a drop-off 412 in delivered stimulation current compared to the normal rectangular waveform 411. Were this voltage non-compliance to go uncorrected, this would result in the delivered charge being less than the intended charge (i.e. by an amount corresponding to the integral of the drop-off 412), with the consequence being that the nerve excitation resulting from the less than intended stimulation charge may result in suboptimal and/or problematic inaccuracies in sensory perception and/or myoelectric activation.

Stimulation circuit 120 is configured to rectify any detected drop-off 412 by providing an extension 414 of the stimulation current for a short period so that the shortfall in delivered charge can be compensated by the charge delivered in current extension 414. As is shown in FIG. 4, this current extension 414 corresponds to a voltage extension 424, allowing the voltages seen at reference capacitors C1 and C2 to converge (following their divergence, which started at point 422 where the voltage Velec started to track below the compliance voltage of the current generator).

Example current pulses 432, 434 and 436 illustrate this effect, where current pulse 432 shows the standard pulse width (i.e. that which is intended to be delivered and which is provided as the reference current pulse at $I_1$). Current pulse 434 shows the current extension signal turning on at a point corresponding to non-voltage-compliance point 422 (or earlier) and extending the provision of charge delivery until the charges at reference capacitors C1 and C2 reconverge. The resultant extended pulse width current signal is shown by reference indicator 436.

Figure 5:
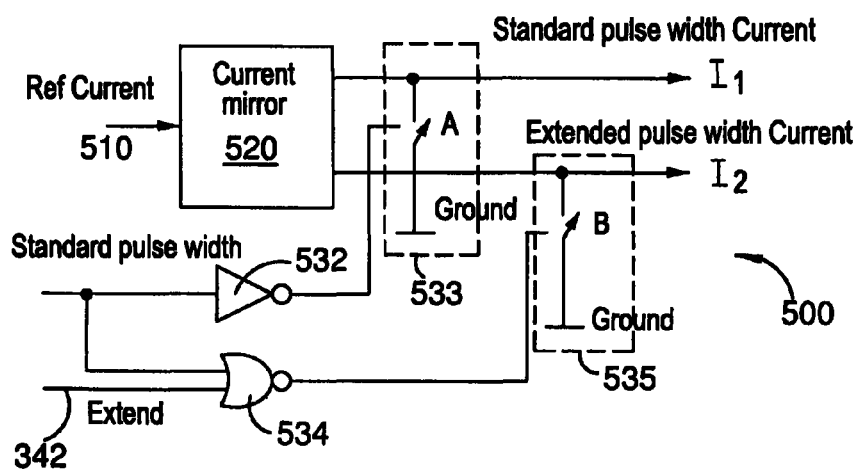
FIG. 5 is a schematic representation of control circuitry for controlling delivery of supplemental charge.
Figure 6:
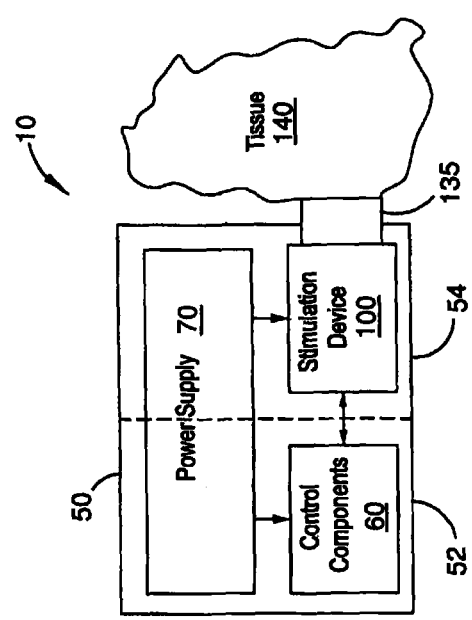
FIG. 6 is a schematic diagram of a stimulation prosthesis including the device and/or circuitry of FIGS. 2, 3 and 5.

Referring now to FIG. 5, a switching circuit 500 is shown and described, where the switching circuit 500 receives the feedback signal 342 from comparator 340 to extend the current pulse width of reference current $I_2$. Switching circuit 500 receives a reference current 510, being the same current that is used to generate reference currents $I_1$ and $I_2$. Reference current 510 is received at a current mirror 520, which provides the same current via separate outputs, as reference currents $I_1$ and $I_2$.

While the standard pulse width signal is high, an inverter 532 causes a switch A of switching circuit 533 to be open, where switching circuit 533 controls whether the standard pulse width current is provided as reference current $I_1$. The standard pulse width high signal is also provided to a NOR gate 534, which also receives the feedback signal 342. In this way, while the standard pulse width signal is high, the NOR gate 534 controls a switch B of switching circuit 535 to be closed to draw the output of the extended pulse width current line to ground. When the standard pulse width signal goes low (i.e. at the trailing edge of 432), inverter 532 closes switch A of switching circuit 533. If the feedback signal 342 goes low to indicate a detected difference in charge between capacitors C1 and C2, the NOR gate 534 causes switch B in switching circuit 535 to be open, with the result being that the standard pulse width current output from current mirror 520 is drawn to ground and the extended pulse width current output is not drawn to ground at the same time and is provided as the reference current $I_2$. If the standard pulse width signal is low and the feedback signal 342 is high to indicate no detected difference in charge between capacitors C1 and C2, then switch B remains closed, drawing the extended pulse width current to ground. It should be understood that the illustrated logic and circuits can be reconfigured so that high and low signal levels described herein can be inverted.

Current switching circuit 500 may effectively form part of stimulation circuit 120, although it is not shown in FIG. 3 for simplicity of illustration. However, in some embodiments, current switching circuit 500 may be considered to form a separate component that cooperates with stimulation circuit 120. In some embodiments, the functions of current switching circuit 500 may be provided by a processor or controller, such as microcontroller 110.

It should be noted that the circuits illustrated in FIGS. 3 and 5 in particular are provided by way of example to illustrate the concept of monitoring the delivered charge and extending the stimulation pulse width as necessary in order to deliver the required charge. Other circuit configurations may be employed in order to achieve a similar effect and it is considered that such variations fall within the scope of the described embodiments. In particular, some variations considered by the inventors to fall within the scope of the described embodiment include implementing the monitoring circuit using a shunt resistor and integrator to, determine the charge delivered to the terminals 305. Alternatively, a large series capacitor could be used as a combined sensing element and integrator. In a further alternative, a sense resistor, analogue to digital converter (ADC) and microcontroller arrangement may be used to determine the charge delivered. Further, a switched capacitor integrator is another alternative arrangement. However, such alternatives may not have the accuracy and low complexity of the example configurations disclosed in detail herein.

In the embodiments described, the stimulation circuit 120 need not be run with as high a supply voltage Vdd as would normally be provided by power supply 70. Rather, instead of being set at 10 volts, which is normal, the supply voltage Vdd could be set at around 5 volts, with the stimulation pulse width being extended if necessary in order to achieve the intended charge delivery, as described herein. Using such a reduced supply of voltage would result in significant power savings for the stimulation device 100 and prosthesis 50, in turn providing substantially improved battery lifetime, where a battery is provided as the power supply 70.

The described embodiments offer a simple way in which the supply voltage of a current source stimulator can be significantly, reduced, while maintaining the desired stimulation levels. On occasions where the supply voltage is insufficient for compliance requirements, the charge is still controlled, but provided at the available supply voltage. Although this may cause some inaccuracy in the level of neural stimulation (although not in charge delivered), this inaccuracy would only apply to a correction component of the charge and not to the full charge. Further, this would only apply to cases where the supply voltage was insufficient for full constant current stimulation. Additionally, the correction component of the charge may include further adjustment according to an empirically derived adjustment model based on known or measured dependency of stimulation efficacy or sensitivity as a function of pulse width or current. The use of such an adjustment model to further modify the charge pulse width would minimise the abovementioned inaccuracy.

Described embodiments may allow new safety studies to be avoided or minimised by use of the described arrangements, because the peak currents are the same as for conventional constant current stimulation.

Where the charge pulses to be delivered using the described device 100, assistive device 50 or system 10 include bi-phasic stimulus pulses, the second phase may be controlled by microcontroller 110 to be the same as the first phase or it may be different. Where the second phase is controlled to be different, it may use a higher current or rely on voltage-driven stimulation, for example. Since described embodiments can extend the total pulse duration (when needed) over what would be required when sufficient voltage is available, having the microcontroller 110 vary the second phase in a way that shortens it compared to the first phase allows the total duration of both phases to be adjusted closer to, or even shortened beyond, the normal total duration. For example, the second phase may include a higher current at a shorter pulse width, capitalising on a lower required voltage in the second phase.

The invention claimed is:

1. A device for generating stimulation signals, comprising:
   a stimulation delivery circuit;
   a first component to monitor charge delivered in at least one charge pulse via the stimulation delivery circuit;
   a second component to ensure delivered charge substantially corresponds to charge of a charge pulse intended to be delivered by the stimulation delivery circuit; and
   a charge setting circuit responsive to a charge pulse waveform to set the charge of the charge pulse intended to be delivered.

2. The device of claim 1, wherein the charge setting circuit comprises a first current mirror circuit coupled to the second component to communicate to the second component the charge of the charge pulse intended to be delivered.

3. The device of claim 1, further comprising a reference capacitor to store the set charge.

4. The device of claim 1, further comprising a comparator to output a difference signal indicative of difference between delivered charge from the stimulation delivery circuit and the charge intended to be delivered.

5. The device of claim 1, wherein the first and second components form at least part of a stimulation supply circuit of the device, wherein the stimulation supply circuit is coupled to provide the at least one charge pulse to the stimulation delivery circuit.

6. The device of claim 1, further comprising a delivered charge capacitor to store charge corresponding to an amount of charge delivered during delivery of the at least one charge pulse.

7. The device of claim 6, further comprising a transistor in series with the delivered charge capacitor and an output of a second current mirror arrangement coupled to a current supply input of the device.

8. The device of claim 1, further comprising a third component responsive to the second component to extend the at least one charge pulse until the intended charge is delivered.

9. A device for generating stimulation signals, comprising:
   a stimulation delivery circuit;
   a monitoring component to monitor charge delivered in at least one charge pulse via the stimulation delivery circuit; and
   a feedback component to provide a feedback signal so that delivered charge substantially corresponds to charge of a charge pulse intended to be delivered by the stimulation delivery circuit;
   wherein the feedback component comprises a charge setting circuit responsive to a charge pulse waveform to set the charge of the charge pulse intended to be delivered.

10. The device of claim 9, wherein the feedback component comprises a comparison circuit, and wherein the charge setting circuit comprises a first current mirror circuit coupled to the comparison circuit to indicate to the comparison circuit the charge of the charge pulse intended to be delivered.

11. The device of claim 10, wherein the comparison circuit comprises a comparator to output a difference signal indicative of difference between delivered charge from the stimulation delivery circuit and the charge intended to be delivered.

12. The device of claim 9, wherein the feedback component comprises a reference capacitor to store the set charge.

13. The device of claim 9, wherein the monitoring component and feedback component form at least part of a stimulation supply circuit of the device, wherein the stimulation supply circuit is coupled to provide the at least one charge pulse to the stimulation delivery circuit.

14. The device of claim 9, further comprising a delivered charge capacitor to store charge corresponding to an amount of charge delivered during delivery of the at least one charge pulse.

15. The device of claim 14, further comprising at least one transistor in series with the delivered charge capacitor and forming part of a second current mirror arrangement coupled to a current supply input of the device.

16. The device of claim 9, further comprising a pulse extension component responsive to the feedback component to extend the at least one charge pulse until the intended charge is delivered.

17. The device of claim 9, further comprising a microcontroller coupled to the device components to control pulse timing and pulse width of the at least one charge pulse.

18. The device of claim 9, wherein the at least one charge pulse forms part of a series of charge pulses to be delivered in charge-balanced pulsatile stimulation.

19. The device of claim 9, wherein the device is configured for use as part of a prosthesis or assistive device.

20. The device of claim 19, wherein the prosthesis is a sensory prosthesis.

21. The device of claim 20, wherein the prosthesis is one of an optic prosthesis and an aural prosthesis.

22. Control circuitry to control delivery of stimulation signals to a stimulus site, comprising:
- monitoring circuitry to monitor charge delivered in at least one charge pulse to an output coupled for delivery of the charge to the stimulus site;
- compliance circuitry cooperating with the monitoring circuitry to ensure delivery of charge intended to be delivered in a charge pulse based on the monitored delivered charge; and
- charge setting circuitry responsive to a charge pulse waveform to set the charge of the charge pulse intended to be delivered.

* * * * *